United States Patent
Pierre et al.

(10) Patent No.: US 8,317,849 B2
(45) Date of Patent: Nov. 27, 2012

(54) PEDIATRIC UNDERBODY BLANKET

(75) Inventors: Joseph Pierre, Libertyville, IL (US);
Rachel Starr, Randolph, MA (US);
Gregory Hughes, Hanson, MA (US)

(73) Assignee: Smiths Medical ASD, Inc., Rockland, MA (US)

( * ) Notice: Subject to any disclaimer, the term of this patent is extended or adjusted under 35 U.S.C. 154(b) by 281 days.

(21) Appl. No.: 12/654,487

(22) Filed: Dec. 22, 2009

(65) Prior Publication Data
US 2011/0152984 A1 Jun. 23, 2011

(51) Int. Cl.
*A61F 7/00* (2006.01)

(52) U.S. Cl. ........................................ 607/107

(58) Field of Classification Search ................ 607/104, 607/107, 108
See application file for complete search history.

(56) References Cited

U.S. PATENT DOCUMENTS

| | | | |
|---|---|---|---|
| 5,300,101 A * | 4/1994 | Augustine et al. | 607/107 |
| 5,674,269 A * | 10/1997 | Augustine | 607/107 |
| 6,102,936 A * | 8/2000 | Augustine et al. | 607/96 |
| 6,581,400 B2 | 6/2003 | Augustine et al. | |
| 6,689,155 B2 | 2/2004 | Gammons et al. | |
| 2008/0021530 A1 | 1/2008 | Castellani et al. | |
| 2008/0053462 A1 | 3/2008 | Teves et al. | |
| 2008/0288034 A1 * | 11/2008 | Pierre et al. | 607/107 |

OTHER PUBLICATIONS

PCT International Search Report and Written Opinion, ISA/KR, Date of mailing Sep. 19, 2011.

* cited by examiner

*Primary Examiner* — Roy Gibson
(74) *Attorney, Agent, or Firm* — Louis Woo

(57) ABSTRACT

An underbody convective warming blanket that may be used by a pediatric or neonate patient includes a head portion configured with multiple substantially U-shaped channels each having a plurality of adjacent rows of apertures that circumscribe the head of the patient positioned on the blanket. The adjacent rows of apertures are configured on the upper layer of the blanket so as to be positioned at an orientation or angle relative to the base plane of the blanket or the head of the patient such that those apertures would substantially face the head of the patient when the blanket is inflated, so that the heated air output from the apertures is directed substantially towards the head of the patient to thereby effect an invisible dome of heated air that envelopes the head of the patient.

21 Claims, 2 Drawing Sheets

US 8,317,849 B2

PEDIATRIC UNDERBODY BLANKET

FIELD OF THE INVENTION

The present invention relates to thermal blankets, and more particularly to an inflatable convective underbody thermal blanket for a pediatric or neonate patient.

BACKGROUND OF THE INVENTION

It is often difficult to maintain the warmth of a pediatric or neonate patient during surgical procedures. This is due to the fact that a large amount of heat from the pediatric patient escapes through the head of the patient. Surgical procedures for pediatric patients oftentimes require that there be unrestricted access to the body of the pediatric patient.

SUMMARY OF THE PRESENT INVENTION

The underbody thermal convective blanket of the instant invention is intended to be used mainly for pediatric or neonate patients, and is configured to focus the heated air output from the blanket to the head of the patient. To that end, the blanket is divided into a head portion and a body portion, with the head portion configured to have a substantial U-shaped channel that includes multiple rows of holes or apertures. When the channel is inflated, the rows of apertures are positioned in such a way that the temperature treated air, for example heated air that is fed into the convective blanket, is output through those apertures substantially directed to the head of the patient. A second substantially U-shaped channel at the head portion of the blanket circumscribes the first U-shaped channel. The second U-shaped channel may also have multiple rows of apertures that are configured to be positioned to direct the temperature treated air output from those apertures in a direction towards the head of the patient when the blanket is inflated. As the U-shaped channels each circumscribe the head of the patient, when the patient is positioned onto the blanket, the temperature treated air output from the U-shaped channels is directed substantially to the top, left and right sides of the head of the patient. Accordingly, an invisible dome of warm air envelopes the head of the patient, thereby keeping the head of the patient warm by counteracting, if not wholly preventing, loss of heat from the head of the patient.

To further ensure that the head of the patient is enveloped by warm air, drapes may be attached to the respective sides at the head portion of the blanket. These drapes may be folded to cover the head of the patient, while the patient is being incubated, so that the heated air output from the substantially U-shaped channels is confined about the head of the patient.

The convective warming blanket of the instant invention has a body portion that includes a non-inflatable body section onto which at least the torso of the patient may be placed. At least one pair of longitudinal channels sandwich the non-inflated body section so that the patient is relatively secured onto the blanket. A plurality of adjacent rows of apertures may be provided at the body portion orthogonal to the length of the blanket just below the head portion of the blanket. These apertures output the temperature treated air to warm the shoulders and the upper torso of the patient.

BRIEF DESCRIPTION OF THE FIGURES

The present invention will become apparent and will best be understood by reference to the following description of the invention taken in conjunction with the accompanying drawings, wherein.

DETAILED DESCRIPTION OF THE INVENTION

Figure 1:
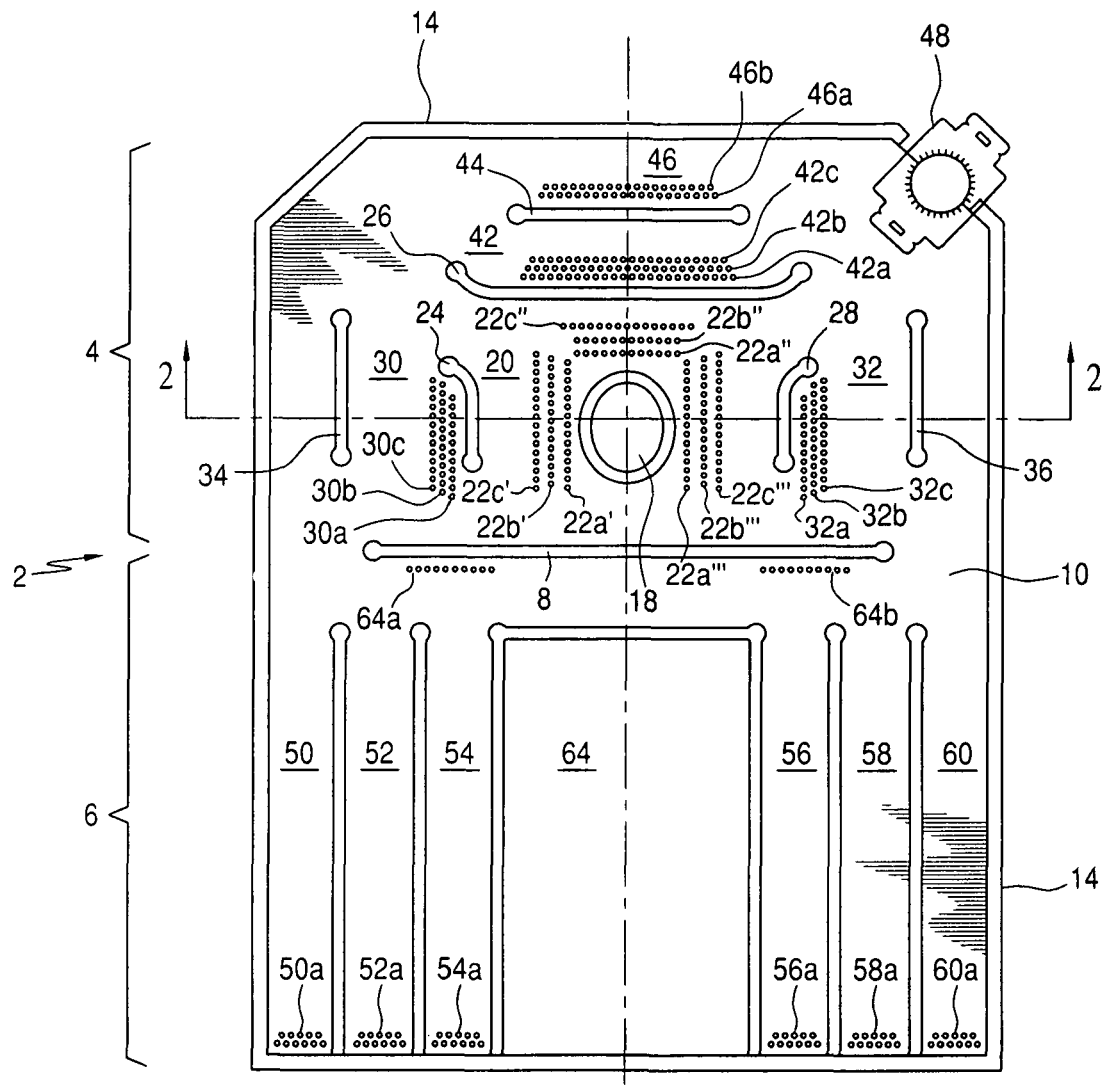
FIG. 1 is a top view of the convective thermal warming blanket of the instant invention.
Figure 2:
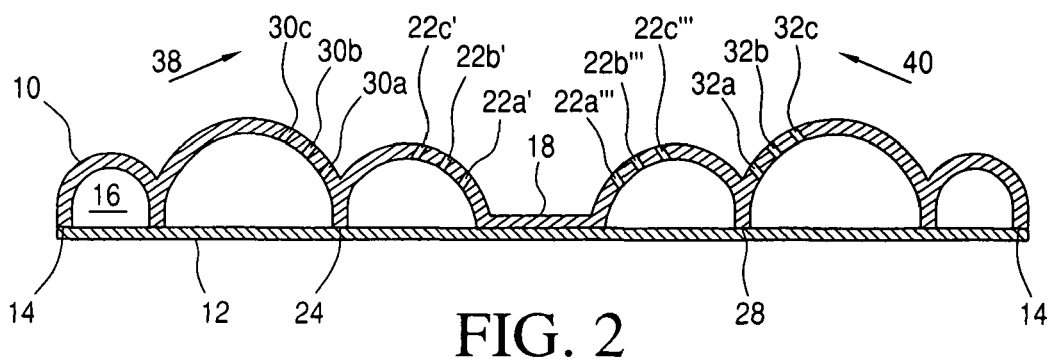
FIG. 2 is a cross-sectional view along section 2-2 of the blanket shown in FIG. 1.

The convective warming thermal blanket 2 shown in FIG. 1 has a head portion 4 and a body portion 6, roughly demarcated by a bonded section 8. As shown in FIG. 2, blanket 2 comprises an upper or top sheet or layer 10 and a bottom or lower sheet or layer 12. Sheets 10 and 12 are air impermeable and are made from a white non-woven polypropylene spunbund extrusion coated material, as is conventionally known. Top sheet 10 is joined to lower sheet 12 at their respective peripheries 14 at all four sides to form an inflatable structure. Sheets 10 and 12 are moreover selectively bonded at different sections, such as the aforenoted section 8, so that those portions of the sheets not bonded form pockets that are inflatable when temperature treated air for example heated air is input to the blanket structure. An exemplar inflated pocket portion is identified as 16 in the cross-sectional view of FIG. 2.

In head portion 4 of blanket 2 there is a non-inflatable head section 18 surrounded by a substantially U-shaped channel 20 in close proximity to three of its sides. As shown in FIG. 1, channel 20 is formed by a plurality of adjacent rows of apertures, identified as 22a (comprising 22a', 22a" and 22a'"), 22b (22b', 22b" and 22b'") and 22c (22c', 22c" and 22c'"), that are respectively positioned adjacent to the non-inflatable head section 18. Holes or apertures 22a', 22a" and 22a'" are made or punched in the top sheet and form a continuous row of apertures that circumscribes the non-inflatable head section 18 at its left, top and right sides, per shown in the top view of FIG. 1. When a patient is placed on top layer 10 of blanket 2, with the head of the patient positioned on the non-inflatable head section 18 and blanket 2 inflated, the apertures from row 22a are positioned at an orientation or angle relative to the base plane of the blanket, or the head of the patient, to substantially face the head of the patient such that the heated air output from those apertures is directed substantially to the right (per apertures 22a'), top (22a") and left (22a'") sides of the head of the patient.

Apertures 22b and 22c making up the other two rows of apertures of channel 20 are shown in the FIG. 1 embodiment blanket to be discontinuous segments, with the rows of apertures 22b' and 22c' to the left side of head section 18, the rows of apertures 22b" and 22c" to the top of head section 18, and the rows of apertures 22b'" and 22c'" to the right side of head section 18. Similar to the apertures of row 22a, the apertures of rows 22b and 22c likewise are configured in close proximity to head section 18 such that when channel 20 is inflated, the apertures of rows 22b and 22c are oriented at an angle to face the head of the patient to thereby direct the heated air output from those apertures to the head of the patient. Inflatable channel 20 in the FIG. 1 embodiment blanket therefore may be defined by the three substantially U-shaped rows of apertures 22a (22a' to 22a'"), 22b (22b' to 22b'") and 22c (22c' to 22c'"), and is substantially confined by bonded sections 24, 26 and 28.

Head portion 4 of blanket 2 further includes two other inflatable channels 30 and 32. Channel 30 is defined between bonded sections 24 and bonded section 34, while channel 32 is defined between bonded section 28 and bonded section 36. At each of channels 30 and 32 there are a plurality of rows of apertures. These rows of apertures are identified as 30a, 30b and 30c for channel 30, and 30a, 32b, 32c for channel 32. The apertures for channel 30 are located adjacent to bonded section 24, whereas the apertures for channel 32 are located adjacent to bonded section 28. The apertures are formed on top layer 10 such that when the blanket structure is inflated, the rows of apertures 30a, 30b and 30c for channel 30 are oriented into a position relative to the base plane of the blanket or the head of the patient such that the apertures would substantially face the head of the patient and the heated air output from those apertures would be directed substantially towards the head of the patient, per the direction indicated by directional arrow 38 in FIG. 2. The same positional orientation relative to the blanket or the head of the patient holds true with respect to the rows of apertures 32a, 32b and 32c in channel 32 when the blanket is inflated. There, apertures 32a, 32b and 32c would substantially face the head of the patient and the air output from those apertures would be directed substantially to the head of the patient along the direction indicated by directional arrow 40, when channel 32 is inflated.

Head portion 4 has another inflatable channel 42 that includes multiple rows of apertures 42a, 42b and 42c. Channel 42 is separated from channel 20 by bonded section 26 for the exemplar blanket of FIG. 1. Similar to the rows of apertures at the other inflatable channels, rows of apertures 42a, 42b and 42c are punched to top sheet 10 and are configured such that when channel 42 is inflated, the air output from those apertures would be directed towards the head of the patient lying on non-inflatable head portion 18.

Yet another channel 46 is defined between periphery 14 and bonded section 44 at the top of head portion 4 for the FIG. 1 blanket. The double rows of apertures 46a and 46b of channel 46 likewise are punched to top sheet 10 and are configured sufficiently adjacent to bonded section 44 such that, due to the positional orientation of the rows of apertures 46a and 46b relative to the base plane of the blanket or the head of the patient when channel 46 is inflated, the rows of apertures 46a and 46b would substantially face the head of the patient and the heated air output from those apertures would be directed substantially towards the head of the patient lying on the uninflated section 18.

Temperature treated air such as heated air is input to inflate the structure of blanket 2 via an inlet 48 by mating a hose (not shown) to the inlet to supply the heated air from a conventionally known air warmer such as the EQUATOR® warmer manufactured by the assignee of the instant invention.

Head portion 4 of the blanket 2 is separated from the body portion 4 by bonded section 8, so that a major portion of the air input to the structure of blanket 2 formed by head portion 4 of the blanket would circulate throughout head portion 4 of the blanket. Given that bonded section 8 does not extend completely to the left and right peripheries of the blanket, heated air also flows to body portion 6 of the blanket to inflate the inflatable channels 50, 52, 54, 56, 58 and 60 extending along the longitudinal axis of blanket 2.

Body portion 6 has a non-inflated section 64 onto which the torso and the feet of the pediatric or neonate patient may be positioned. The sets of plurality of apertures 50a, 52a, 54a, 56a, 58a and 60a at the foot end of the blanket for the respective channels 50, 52, 54, 56, 58 and 60 allow air to escape from the blanket, so that those longitudinal channels may be inflated and warmed. At least one discontinuous row of apertures 64a and 64b is provided adjacent to bonded section 8 at body section 6 for outputting air to the shoulders and the upper torso of the patient, when the patient is positioned on blanket 2.

Figure 3:
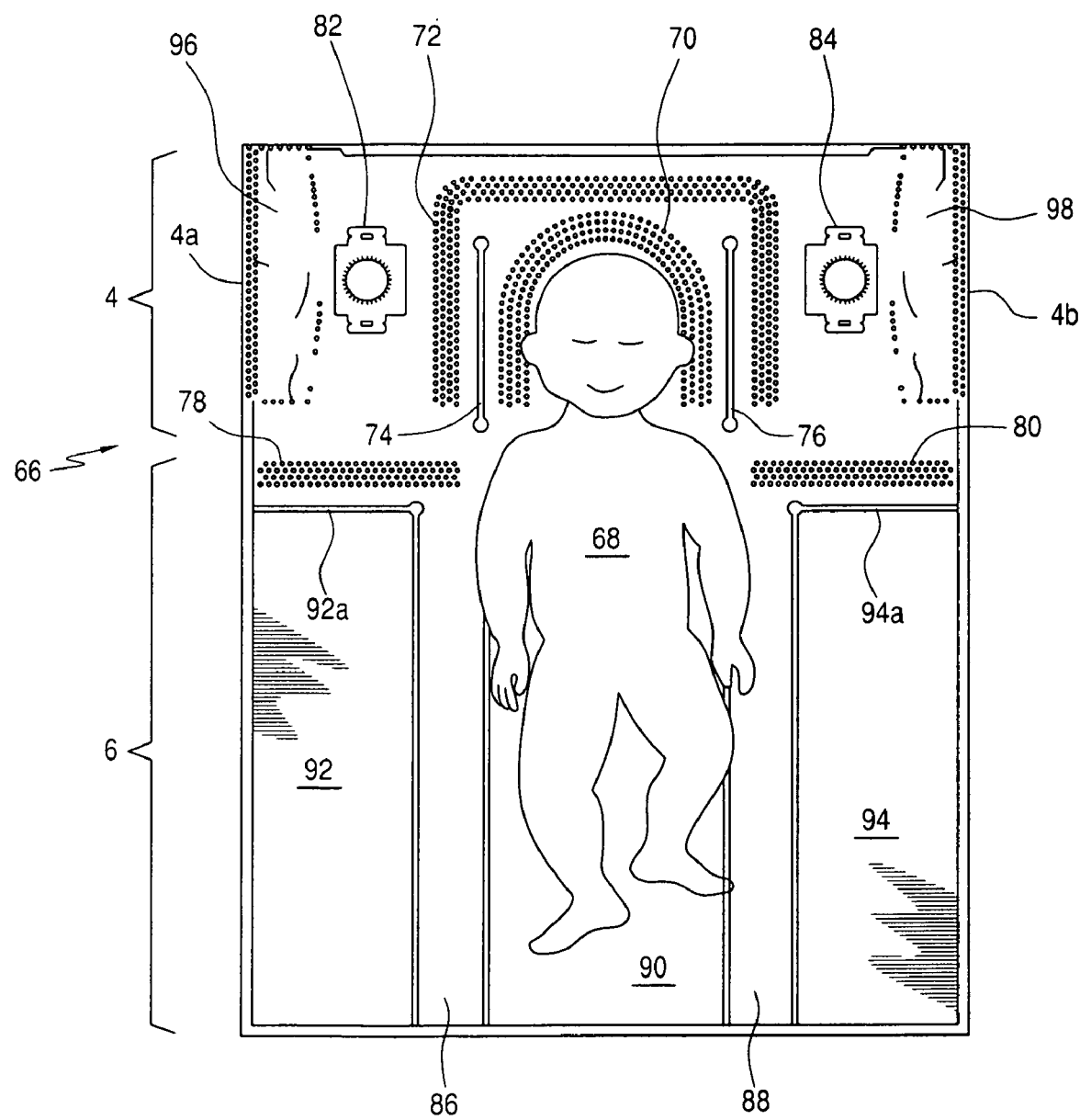
FIG. 3 shows an alternative embodiment of the blanket of the instant invention with a patient positioned thereon for illustration purposes.

FIG. 3 is an illustration of an alternate embodiment blanket of the instant invention. As shown, blanket 66 also has a head portion 4 and a body portion 6, and is made of a top layer joined to a bottom layer at their respective peripheries and also at selected bonded sections to effect an inflatable structure for supporting a patient such as a pediatric or neonate patient 68.

Head portion 4 of blanket 66 has a U-shaped channel 70 that is made up of multiple adjacent rows of apertures. For the exemplar blanket shown in FIG. 3, there are four adjacent rows of apertures in close proximity to and circumscribing the non-inflatable section (blocked by the head of the patient as shown in FIG. 3) onto which the head of patient 68 rests. For the FIG. 3 embodiment blanket, the multiple adjacent rows of apertures may simply be referred to as inflatable channel 70.

Head portion 4 further has another substantially U-shaped channel 72 formed by another set of multiple adjacent rows of apertures or holes formed on the top layer of the blanket structure. The left and right portions of channel 72 are separated from the left and right portions of channel 70 by bonded sections 74 and 76, respectively. The respective positional orientations of the multiple rows of apertures for both channels 70 and 72 relative to the plane of the main body of the blanket or the head of the patient, when blanket 66 is inflated, are such that those apertures would substantially face the head of the patient and the heated air output from those rows of apertures is directed substantially to the head of the patent, particularly towards the top, left and right sides of the patient's head.

Two other channels of apertures, designated 78 and 80, at the respective left and right sides of blanket 66 output heated air to the shoulders and upper torso of the patient. By locating the multiple rows of apertures 78 and 80 at the upper end of body section 6, most of the heated air input to the blanket structure is output and directed to the upper portion of the patient and more particularly towards the head of the patient to thereby maintain an invisible dome of heated air over the head of the patient, where most of the heat of the patient would otherwise escape.

The exemplar blanket shown in FIG. 3 includes a pair of inlets 82 and 84 at the head portion 4. As is conventionally known, only one of inlets 82 and 84 is used for connection to the hose (not shown) of an air warmer such as the aforenoted EQUATOR® warmers, so that heated air may be input through the selected inlet for inflating blanket 66 with the temperature treated air.

Body portion 6 of blanket 66 is configured to have two inflatable channels 86 and 88 that sandwich a non-inflated section 90 whereon the torso of the patient lies. To the respective sides of the channels 86 and 88 are flaps 92 and 94 that are formed from sealed sections of the top and bottom layers of blanket 66. Each of flaps 92 and 94 is separable from the main body (non-inflatable section 90 and channels 86 and 88) of body portion 6 of the blanket per cuts or weakened sections 92a and 94a, respectively, so that flaps 92 and 94 each may be folded over the torso, and also conceivably the legs, of the patient to thereby cover the patient.

There are in addition two drapes 96 and 98 attached to the respective sides of head portion 4, at the respective peripheries 4a and 4b thereof, so that each of those drapes 96 and 98 may be folded over the head of the patient to maintain the heated air output from the channels of apertures over the head of the patient, for example when the patient is incubated. Drapes 96 and 98 may be made of a transparent plastic material to enable the medical personnel to continuously monitor the head of the patient.

The invention as disclosed above is subject to many variations, modifications and changes in detail. For example, even though blanket 2 of FIG. 1 is not shown with any drapes for head portion 4, it nonetheless should be understood that head drapes such as 96 and 98 for the exemplar blanket of FIG. 3 may also be added to the respective sides at the head portion of the exemplar FIG. 1 blanket. Further, even though particular rows of apertures are shown for the respective blankets, it should be appreciated that instead of the three adjacent rows of apertures as shown for channel 20 of blanket 2, additional rows or a small number of rows of apertures may be formed instead. The same is true with respect to the other multiple rows of apertures shown for each of blankets 2 and 66 as discussed above. Furthermore, even though one inlet is shown for the exemplar blanket of FIG. 1, in practice the blanket of the instant invention may be equipped with two inlets to enhance its usability. Accordingly, it is intended that the invention be limited only by the spirit and scope of the hereto appended claims.

The invention claimed is:

1. A convective blanket for supporting a patient, comprising:
   a top layer for supporting the body of the patient;
   a bottom layer joined to the top layer at its periphery, said top and bottom layers selectively bonded at different sections away from the periphery to form an inflatable structure where portions of said top and bottom layers not bonded form pocketed portions that are inflatable;
   at least one input port provided at said inflatable structure whereby temperature treated air is feedable into said structure;
   wherein said structure is configured to have a head portion including a non-inflatable head section whereon the head of the patient rests when the patient is positioned on said top layer of the structure;
   wherein said non-inflatable head section is surrounded on its three sides that are respectively adjacent to the top, left and right sides of the head of the patient, when the patient is positioned on said top layer, by a substantially U-shaped channel having at least one continuous row of apertures being in close proximity to the top, left and right sides of the non-inflatable head section whereon the head of the patient rests; and
   wherein when said structure is inflated, the apertures of said at least one row are positioned relative to the head of the patient such that the temperature treated air input to said structure is output from the apertures substantially towards the head of the patient.

2. Blanket of claim 1, wherein said head portion further comprises at least two other inflatable channels one on each of the left and right sides of the head of the patient and separated from the left and right sides of said U-shaped channel by corresponding bonded sections of said structure, at least one second row of apertures at each of said two other channels for outputting the temperature treated air substantially towards the head of the patient when said structure is inflated.

3. Blanket of claim 2, further comprising a third channel separated from the top of said U-shaped channel by another bonded section, said third channel having at least one row of apertures for outputting the temperature treated air substantially towards the top of the head of the patient when said structure is inflated.

4. Blanket of claim 3, further comprising a fourth channel located between the periphery of said structure and said third channel above the top of the head of the patient, said fourth channel having at least one row of apertures for outputting the temperature treated air substantially towards the top of the head of the patient when said structure is inflated.

5. Blanket of claim 1, wherein said head portion further comprises at least one U-shaped row of apertures at said head portion circumscribing said U-shaped channel, said U-shaped row of apertures outputting the temperature treated air substantially towards the head of the patient when said structure is inflated.

6. Blanket of claim 1, wherein said U-shaped channel is circumscribed by a plurality of U-shaped rows of apertures at said head portion, the row of apertures at said U-shaped channel and said plurality of U-shaped rows of apertures outputting the temperature treated air to substantially envelope the head of the patient when said structure is inflated.

7. Blanket of claim 1, further comprising another input port;
   wherein said one and another input ports are located at the right and left sides, respectively, of the head portion of the structure.

8. Blanket of claim 1, further comprising at least one drape attached to a section of the periphery at the head portion of said structure, said drape foldable over the head of the patient to maintain the temperature treated air about the head of the patient.

9. Blanket of claim 1, further comprising at least one row of apertures orthogonal to the length of said structure at approximately the shoulder area of the patient, when the patient is positioned on said top layer.

10. Blanket of claim 1, further comprising a non-inflatable body section at a body portion of said structure where the torso and feet of the patient are positioned, a plurality of longitudinal channels extending from a foot end of said structure along the body portion, and a plurality of apertures proximate to the foot end at each of the longitudinal channels for outputting the temperature treated air.

11. A convective blanket comprising:
   a top layer and a bottom layer joined to each other at their respective peripheries to form an inflatable structure, said top and bottom layers selectively bonded at different sections to form selectively inflatable pocketed portions for said structure, said top layer of said structure supporting a patient positioned thereon;
   wherein said structure is configured to have a head portion and a body portion, said head portion including a non-inflatable head section whereon the head of the patient rests when the patient is positioned on said top layer;
   wherein said non-inflatable head section is surrounded on its three sides that are respectively adjacent to the top, left and right sides of the head of the patient, when the patient is positioned on said top layer, by a substantially U-shaped channel defined by a plurality of rows of apertures having at least one continuous row of apertures being in close proximity to the non-inflatable head section whereon the head of the patient rests; and
   wherein when said structure is inflated, the rows apertures of said U-shaped channel are positioned relative to the head of the patient such that the temperature treated air input to said structure is output from the apertures substantially towards the head of the patient.

12. Blanket of claim 11, wherein said head portion further comprises at least two other inflatable channels one on each of the left and right sides of the head of the patient and separated from the left and right sides of said U-shaped channel by a corresponding bonded section of said structure, a plurality of second rows of apertures at each of said two other channels for outputting the temperature treated air substantially towards the head of the patient when said structure is inflated.

13. Blanket of claim 12, further comprising a third channel separated from the top of said U-shaped channel by another bonded section, said third channel having a third plurality of rows of apertures for outputting the temperature treated air substantially towards the top of the head of the patient when said structure is inflated.

14. Blanket of claim 13, further comprising a fourth channel located between the periphery of said structure and said third channel above the top of the head of the patient, said fourth channel having a fourth plurality of rows of apertures for outputting the temperature treated air substantially towards the top of the head of the patient when said structure is inflated.

15. Blanket of claim 11, further comprising at least one row of apertures at the body portion separated into two discontinuous sections orthogonal to the length of said structure at approximately the shoulder area of the patient, when the patient is positioned on said top layer.

16. Blanket of claim 11, further comprising a non-inflatable body section at the body portion of said structure where the torso and feet of the patient are positioned, said non-inflatable body section sandwiched by at least one pair of longitudinal channels extending from a foot end of said structure along the body portion.

17. A convective blanket comprising:
a top layer and a bottom layer joined to each other at their respective peripheries to form an inflatable structure, said top and bottom layers selectively bonded at different sections to form selectively inflatable pocketed portions for said structure, said top layer of said structure supporting a patient positioned thereon;
wherein said structure is configured to have a head portion and a body portion, said head portion including a non-inflatable head section whereon the head of the patient rests when the patient is positioned on said top layer;
wherein said non-inflatable head section is surrounded on its three sides that are respectively adjacent to the top, left and right sides of the head of the patient, when the patient is positioned on said top layer, by two spaced apart substantially U-shaped channels each defined by at least one row of apertures; and
wherein when said structure is inflated, the respective at least one rows of apertures of said U-shaped channels are positioned relative to the head of the patient such that the temperature treated air input to said structure is output from the apertures substantially towards the head of the patient.

18. Blanket of claim 17, wherein each of said U-shaped channels comprises a plurality of rows of apertures for outputting the temperature treated air substantially towards the head of the patient when said structure is inflated.

19. Blanket of claim 17, further comprising another input port;
wherein said one and another input ports are located at the right and left sides, respectively, of the head portion of the structure.

20. Blanket of claim 17, further comprising at least one drape attached to a section of the periphery of the structure at the head portion of said structure, said drape foldable over the head of the patient to maintain the temperature treated air about the head of the patient.

21. Blanket of claim 17, wherein said body portion comprises a main body and two non-inflatable sections that are detachable from and foldable over the main body of said body portion.

* * * * *